United States Patent
Hossack et al.

(10) Patent No.: US 9,445,780 B2
(45) Date of Patent: Sep. 20, 2016

(54) TRACKED ULTRASOUND VESSEL IMAGING

(75) Inventors: John A. Hossack, Charlottesville, VA (US); Michael I. Fuller, Charlestown, MA (US); Travis N. Blalock, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1347 days.

(21) Appl. No.: 12/960,477

(22) Filed: Dec. 4, 2010

(65) Prior Publication Data

US 2011/0137175 A1    Jun. 9, 2011

Related U.S. Application Data

(60) Provisional application No. 61/266,784, filed on Dec. 4, 2009.

(51) Int. Cl.
| | | |
|---|---|---|
| A61B 8/00 | (2006.01) | |
| A61B 8/08 | (2006.01) | |
| G01S 7/52 | (2006.01) | |
| G01S 15/89 | (2006.01) | |

(52) U.S. Cl.
CPC ............. *A61B 8/0891* (2013.01); *A61B 8/085* (2013.01); *A61B 8/463* (2013.01); *A61B 8/469* (2013.01); *A61B 8/523* (2013.01); *G01S 7/52046* (2013.01); *G01S 7/52061* (2013.01); *G01S 15/8909* (2013.01); *G01S 15/8993* (2013.01)

(58) Field of Classification Search
None
See application file for complete search history.

(56) References Cited

U.S. PATENT DOCUMENTS

| | | | |
|---|---|---|---|
| 5,575,286 A | 11/1996 | Weng et al. | |
| 5,769,079 A | 6/1998 | Hossack | |
| 5,782,768 A * | 7/1998 | Hashimoto et al. | .......... 600/443 |
| 6,014,473 A | 1/2000 | Hossack et al. | |
| 6,068,599 A | 5/2000 | Saito et al. | |
| 6,190,321 B1 | 2/2001 | Pang et al. | |
| 6,423,006 B1 | 7/2002 | Banjanin | |

(Continued)

FOREIGN PATENT DOCUMENTS

WO    WO-2005055141 A1    6/2005

OTHER PUBLICATIONS

Fuller, M. I, et al., "Real time imaging with the Sonic Window: A pocket-sized, C-scan, medical ultrasound device", 2009 IEEE International Ultrasonics Symposium (IUS), (2009), 196-199.

(Continued)

*Primary Examiner* — Amanda Lauritzen Moher
(74) *Attorney, Agent, or Firm* — Schwegman Lundberg & Woessner, P.A.

(57) ABSTRACT

A medical imaging apparatus, such as including a processor circuit, can be used to construct a first image of a plane parallel to the surface of an ultrasonic imaging transducer, the plane corresponding to a locus at a specified depth within a first region of tissue. The apparatus can obtain information about a location of a vessel in the first image, then obtain, from a second region of tissue, imaging information corresponding to loci in planes parallel to the surface of the transducer, the planes at depths automatically determined at least in part using the obtained information about the location of the vessel in the first image. In an example, the apparatus can automatically determine an adjusted depth corresponding to the location of the vessel in the second region, and construct a second image of a plane corresponding to the adjusted depth within the tissue.

35 Claims, 7 Drawing Sheets

(56) References Cited

U.S. PATENT DOCUMENTS

| | | | |
|---|---|---|---|
| 7,074,187 B2* | 7/2006 | Selzer | A61B 5/02007 600/440 |
| 7,402,136 B2 | 7/2008 | Hossack et al. | |
| 7,699,776 B2 | 4/2010 | Walker et al. | |
| 7,750,537 B2 | 7/2010 | Hossack et al. | |
| 2005/0154303 A1* | 7/2005 | Walker et al. | 600/443 |
| 2006/0052697 A1 | 3/2006 | Hossack et al. | |
| 2006/0100516 A1 | 5/2006 | Hossack et al. | |
| 2007/0016022 A1 | 1/2007 | Blalock et al. | |
| 2007/0016044 A1 | 1/2007 | Blalock et al. | |
| 2009/0048519 A1 | 2/2009 | Hossack et al. | |
| 2010/0063399 A1 | 3/2010 | Walker et al. | |
| 2010/0268086 A1 | 10/2010 | Walker et al. | |
| 2011/0166451 A1* | 7/2011 | Blaivas et al. | 600/439 |
| 2011/0255762 A1* | 10/2011 | Deischinger et al. | 382/131 |
| 2012/0035477 A1* | 2/2012 | Tashiro | 600/443 |

OTHER PUBLICATIONS

Kasai, C., et al., "Real-Time Two-Dimensional Blood Flow Imaging Using an Autocorrelation Technique", IEEE Transactions on Sonics and Ultrasonics, vol. SU-32, No. 3, (1985), 953-958.

* cited by examiner

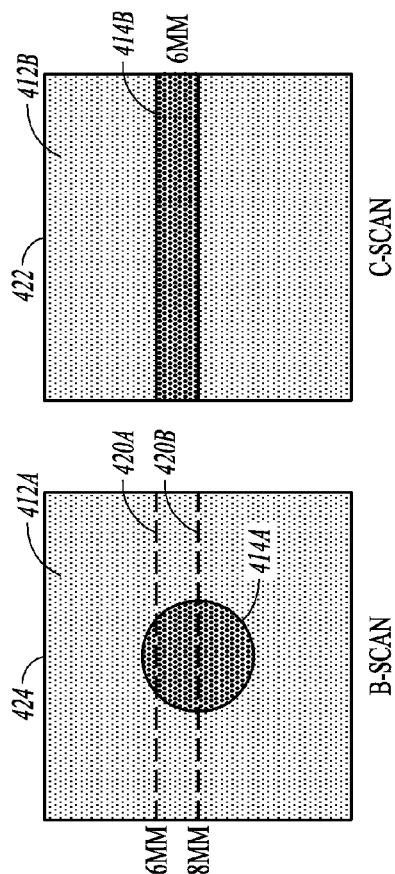
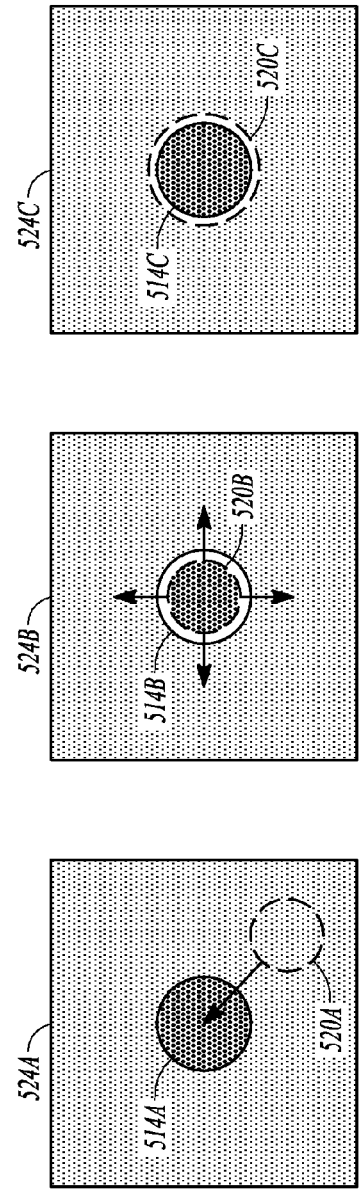
FIG. 4
FIG. 5A  FIG. 5B  FIG. 5C

TRACKED ULTRASOUND VESSEL IMAGING

CLAIM OF PRIORITY

This patent application claims the benefit of priority, under 35 U.S.C. Section 119(e), to Hossack et al., U.S. Provisional Patent Application Ser. No. 61/266,784, entitled "Tracked C-scan Ultrasound Vessel Imaging System and Related Method," filed on Dec. 4, 2009, which is hereby incorporated by reference herein in its entirety.

STATEMENT REGARDING FEDERALLY SPONSORED RESEARCH OR DEVELOPMENT

This invention was made with government support under RR020834 awarded by the National Institutes of Health. The government has certain rights in the invention.

BACKGROUND

Ultrasound imaging can provide clinically-useful information to caregivers. Such information can be used in real-time to assist in visualizing underlying anatomy during a variety of medical procedures. For example, without imaging, a needle insertion can generally involve palpation of vessels in combination with reliance upon general anatomical knowledge. Generally, a needle is to be inserted into a vein without accidentally penetrating any nearby pulsatile arteries. Commonly-accessed veins include the jugular vein, a subclavian vein, or a brachial vein, for example. Use of ultrasound imaging can reduce risk and can increase the confidence of the caregiver that the observed vessel is the intended target vessel, prior to needle insertion, as compared to reliance on palpation or general anatomical knowledge.

Overview

The present inventors have recognized, among other things, that a C-scan ultrasound imaging system can be used to assist in visualizing one or more blood vessels, such as for use as a guidance tool for a needle insertion procedure. The term "C-scan" generally refers to an ultrasound imaging system configured to provide an image of a plane parallel to the face of an ultrasound transducer array (e.g., a matrix of transducers extending in two directions), such as including a target locus at a specified depth or distance away from the face of the transducer array. In contrast, the term "B-scan" generally refers to an ultrasound imaging system configured to provide an image of a plane perpendicular to the face of an ultrasound transducer array (e.g., a linear array of transducers).

Generally, a C-scan imaging system can be used to scan a range of depths, such as until the C-scan plane becomes centered in depth with respect to a targeted vessel (e.g., a vein targeted for a needle insertion). Then, to achieve high confidence that the scanned vessel is the intended target vessel, the C-scan imaging system can be used to scan along the length of the vessel in the vicinity of the targeted needle insertion site. Such depth searching can include scanning a range of depths, such as manually with the assistance of a user (e.g., a caregiver).

For example, such scanning can continue until a distinct vessel image can be observed in which the displayed cross-sectional width appears to be maximized (e.g., corresponding to a plane approximately intersecting the central axis of the vessel). The targeted vessel's depth with respect to the skin surface will likely be non-uniform as the scanner is moved around the surface of the skin, such as along the length of the vessel. Generally, the depth search can be repeated so as to continually or repetitively acquire a plane through the central axis of the intended vessel. The present inventors have recognized, among other things, that such a repetitive search for the vessel depth is a tedious task that can be automated, or at least computer-assisted. The present subject matter is related to automated methods, apparatus, or computer program products (e.g., including a processor-readable medium) for determining an adjusted (e.g., corrected) C-scan depth.

A medical imaging apparatus, such as including a processor circuit, can be used to construct a first image of a plane parallel to the surface of an ultrasonic imaging transducer, the plane corresponding to a locus at a specified depth within a first region of tissue. The apparatus can obtain information about a location of a vessel in the first image, then obtain, from a second region of tissue, imaging information corresponding to loci in planes parallel to the surface of the transducer, the planes at depths automatically determined at least in part using the obtained information about the location of the vessel in the first image. In an example, the apparatus can automatically determine an adjusted depth corresponding to the location of the vessel in the second region, and construct a second image of a plane corresponding to the adjusted depth within the tissue.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 4 illustrates generally an illustrative example of side-by-side imaging information including both B-scan and C-scan ultrasound imaging information that can include a portion of a vessel, such as for graphical presentation to a user.

FIGS. 5A-C illustrate generally an illustrative example that can include a repositionable or resizable indicator that can be manipulated by a user, such as to provide positional information about a vessel to an ultrasound imaging apparatus, such as including information about a depth of a vessel.

DETAILED DESCRIPTION

Figure 1:
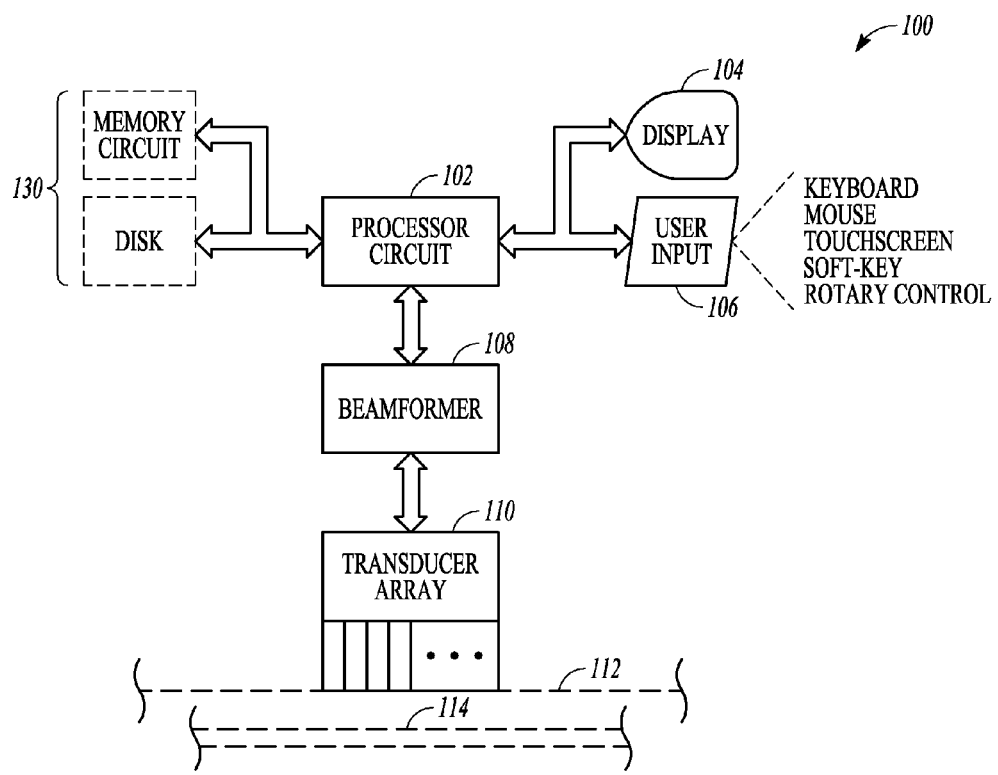
FIG. 1 illustrates generally an example of an apparatus that can include an ultrasonic transducer array.

FIG. 1 illustrates generally an example of an apparatus 100 that can include an ultrasonic transducer array 110. In an example, the ultrasonic transducer array 110 can be placed in contact with a surface 112 (e.g., skin) of a patient. The ultrasonic transducer array 110 can be used such as to insonify a region of tissue below the surface 112, such as to assist in locating or visualizing a vessel 114. Such location or visualization can be used to aid a caregiver in guiding a needle to a targeted vessel, such as prior to insertion of the needle.

Figure 2:
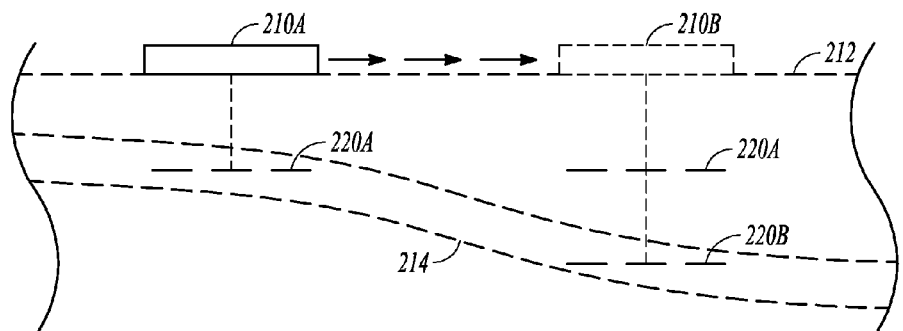
FIG. 2 illustrates generally an example of a vessel located below the surface of an imaging subject's skin, the vessel including a depth that varies along a long axis of the vessel.

In the example of FIG. 1, the transducer array 110 can be coupled to beamforming circuitry or other processing circuitry, such as a beamformer 108. The beamformer 108 can be configured to amplify, phase-shift, time-gate, filter, or otherwise condition imaging information, such as provided to a processor circuit 102. For example, the receive path from each element in the transducer array 110 can include one or more of a low noise amplifier, a main-stage amplifier, a band-pass or a low-pass filter, or an analog to digital converter. In an example, one or more signal conditioning steps can be performed digitally, such as using the processor circuit 102. The term processor is used to generically refer to digital circuitry that can be used to manipulate ultrasound imaging information. Such circuitry can include one or more of a field-programmable gate array (FPGA) or other programmable logic devices (PLDs), a microprocessor, a system-on-chip including one or more execution cores or other circuitry, a microcontroller, or one or more or other circuits. In an example, the apparatus 100 of FIG. 1 can be configured to obtain imaging information from loci corresponding to one or more planes parallel to the surface of the ultrasound transducer array 110 (e.g., to provide a "C-Scan" ultrasound image of loci in a plane parallel to the surface of the transducer array 110 at a specified depth within the tissue 112), such as shown in the example of FIG. 2.

Referring to FIG. 1, in an example, the processor circuit 102 can be coupled to one or more processor readable media 130, such as a memory circuit, a disk, or one or more other memory technology or storage devices. In an example, a combination of one or more of the transducer array 110, the beamformer 108, the processor circuit 102, processor-readable media 130, a display 104, or a user input 106 can be included as a portion of a hand-held ultrasound imaging apparatus, such as including a two-dimensional array of ultrasound transducer elements. For example, such apparatus 100 can include apparatus or circuitry shown and described in Fuller, M. I., Owen, K., Blalock, T. N., Hossack, J. A., and Walker, W. F., "Real time imaging with the Sonic Window: A pocket-sized, C-scan, medical ultrasound device," 2009 IEEE International Ultrasonics Symposium (IUS), Sep. 2009, pp. 196-199, which is hereby incorporated by reference herein in its entirety, including its discussion of a compact, integrated 60 element×60 element ultrasonic transducer array configured to both insonify tissue and receive echo information from the tissue.

Other examples of apparatus or circuitry that can be included as a portion of the apparatus 100, or one or more techniques that can be used in relation to the apparatus 100, can be found in one or more of Walker, W. F., et al., United States Patent Application Publication US2010/0268086, "Intuitive Ultrasonic Imaging System and Related Method Thereof," or Walker, W. F., et al., United States Patent Application Publication US2010/0063399, "Front End Circuitry for Imaging Systems and Methods of Use," or Hossack, J. A., et al., United States Patent Application Publication US2009/0048519, "Hybrid Dual Layer Diagnostic Ultrasound Transducer Array" (issued as U.S. Pat. No. 7,750,537), or Blalock, T. N., et al., United States Patent Application Publication US 2007/0016044, "Ultrasonic Transducer Drive," or Blalock, T. N., et al., United States Patent Application Publication US2007/0016022, "Ultrasound Imaging Beam-Former Apparatus and Method," or Hossack, J. A., et al., United States Patent Application Publication US2006/0100516, "Efficient Architecture for 3D and Planar Ultrasonic Imaging—Synthetic Axial Acquisition and Method thereof," or Hossack, J. A., et al., United States Patent Application Publication US2006/0052697, "Efficient Ultrasound System for Two-Dimensional C-scan Imaging and Related Method thereof," (issued as U.S. Pat. No. 7,402,136), or Walker, W. F., United States Patent Application Publication US2005/0154303, "Intuitive Ultrasonic Imaging System and Related Method thereof" (issued as U.S. Pat. No. 7,699,776), all of which are hereby incorporated by reference herein in their respective entireties.

In an example, the processor circuit 102 (or one or more other processor circuits) can be communicatively coupled to one or more of the user input 106, or the display 104. For example, the user input 106 can include one or more of a keypad, a keyboard (e.g., located near or on a portion of ultrasound scanning assembly, or included as a portion of a workstation configured to present or manipulate ultrasound imaging information), a mouse, a touch-screen control, a rotary control (e.g., a knob or rotary encoder), or a soft-key aligned with a portion of the display 104, or including one or more other controls.

In an example, a system can include a first processor circuit 102, such as configured to control one or more of the beamformer 108 or transducer array 110. The system can include a second processor circuit, such as configured as an imaging post-processor, such as included as a portion of the workstation configured to present or manipulate ultrasound imaging information. For example, the second processor circuit can be configured to obtain imaging information from the first processor circuit 102 or from the one or more processor readable media 130 (or via a wired or wireless network or other interface), such as to present the information to a user (e.g., a caregiver) via a display, or obtain information from the user via a user input.

In an example, the processor circuit 102 can be configured to construct one or more images (e.g., a set of two-dimensional or three-dimensional representations of the vessel 114), such as using imaging information obtained using the ultrasonic transducer array 110. The processor circuit 102 can present the constructed image to the user via the display 104, such as presenting an image including one or more features or indicia as shown in the examples of FIG. 2, 3A-C, 4, 5A-C, 6A-D, 7, or 8A-B, below. The apparatus can generally include a two-dimensional ultrasonic imaging array since such an array can be compact and cost-effectively fabricated using solid state circuitry. However, other techniques can include using a single transducer scanned in two dimensions or a one-dimensional array scanned in the array's elevation dimension, such as to provide imaging information similar to the information provided by a two-dimensional array.

FIG. 2 illustrates generally an example of a vessel 214, such as located below the surface of an imaging subject's skin 212, the vessel having a depth from the surface of the skin that can vary along a long axis of the vessel. In an example, a user (e.g., a caregiver) can use an ultrasound imaging system to assist in locating or visualizing the vessel 214, such as using at least a portion of the apparatus shown in the example of FIG. 1. Such location or visualization can help aid the caregiver in inserting a needle into a desired target vessel. Generally, the needle is to be inserted into a vein without accidentally penetrating any nearby pulsatile arteries. Commonly-accessed veins include the jugular vein, a subclavian vein, or a brachial vein, for example. In the example of FIG. 2, showing a simplified elevation view, an ultrasonic imaging transducer 210A can be placed in contact with the skin 212, such as in a first region. Ultrasonic imaging information can be obtained, such as to provide (e.g., construct and present) a first image of the vessel 214. In an example, the image can be a C-scan (e.g., C-mode) image of a plane corresponding to loci at a specified depth 220A below the skin 212 surface, the C-scan plane generally parallel to the face of the ultrasound imaging transducer 210A.

Generally, to obtain the first image of the vessel 214, the location of the imaging transducer 210A can be adjusted by the user, or otherwise moved across the surface of the skin 212, such as to a location at or near a desired needle insertion site. In an example, a user input can be used to vary the imaging depth until a long-axis vessel view is obtained showing the maximum observed distance between the opposite side walls of the targeted vessel 214 (e.g., as shown in the example of FIG. 3B). In one approach, in a manually-tracking ultrasound imaging system, the ultrasound imaging transducer 210A can then be moved to a second tissue region 210B, laterally offset from the first region. In the second region, in such a manual approach, the depth of the C-scan imaging plane must be again manually adjusted by the user from a first specified depth 220A, to a second specified depth 220B, such as to re-center the C-scan plane within the cross-section of the vessel 214, in the second tissue region. Such manual adjustment can be tedious or time-consuming. In another example, a subsequent tissue region to be imaged can be offset in depth from the first region (e.g., as the skin 212 is compressed), also resulting in a different depth of the vessel 214 relative to the transducer, similar to the situation where the vessel depth varies along its long axis.

The present inventors have recognized, among other things, that the second specified depth 220B, in the second region, can be automatically determined, such as using the apparatus of FIG. 1 or one or more techniques discussed in the examples below of FIG. 3A-C, 4, 5A-C, 6A-D, 7, or 8A-B, such as including being guided by or using information provided by the user about the vessel 214 location in the first tissue region. Thus, as the imaging transducer 210A is moved along the surface of the skin 212, the imaging apparatus can automatically track the depth of the vessel 214, such as moving a C-scan imaging plane automatically from the first depth 220A to a second depth 220B, or one or more other locations roughly following the path of the center of the long axis of the vessel.

Figure 3A:
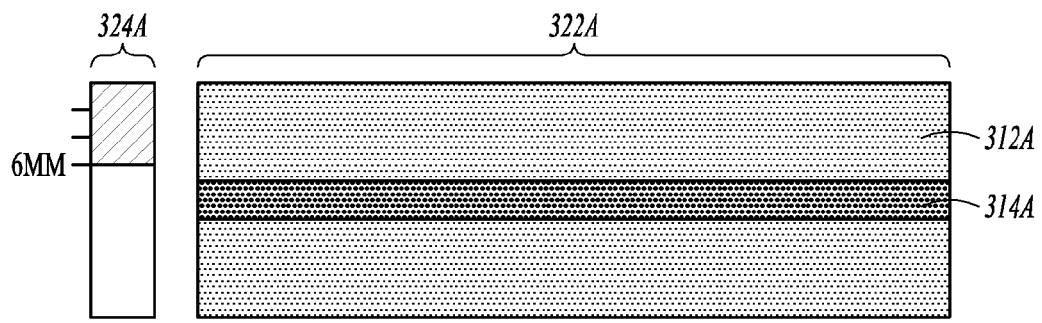
FIG. 3A-C illustrate generally illustrative examples of C-scan ultrasound imaging information including a portion of a vessel, such as for graphical presentation to a user, such as corresponding to a variety of different scanned depths.
Figure 3B:
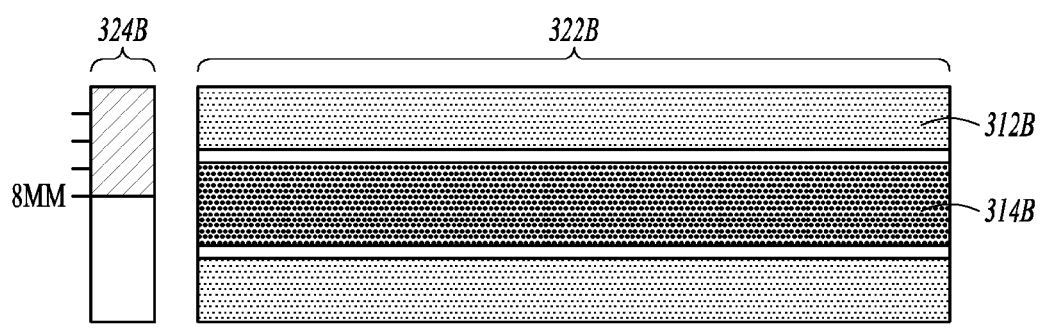
Figure 3C:
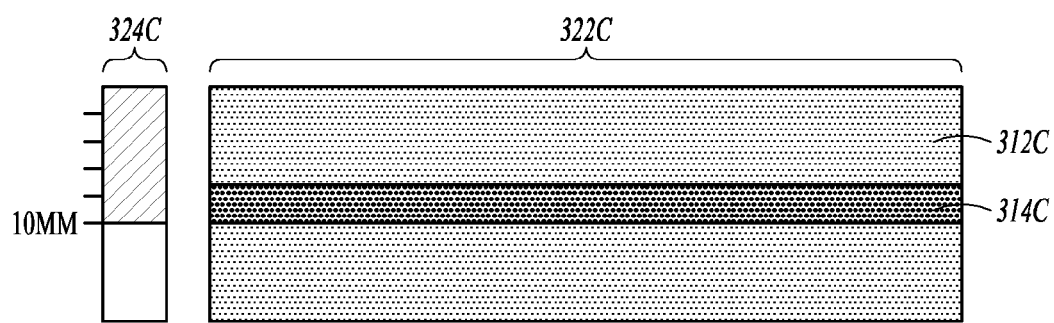

FIG. 3A-C illustrate generally illustrative examples of C-scan ultrasound imaging information that can include a portion of a vessel, such as for graphical presentation to a user, such as including constructed images 322A-C corresponding to a variety of different scanned depths. As discussed above in the examples of FIGS. 1-2, the depth of a C-scan imaging plane can be automatically adjusted, such as to track a depth of a targeted vessel using an external C-scan ultrasound imaging transducer. Generally, ultrasonic imaging information, such as provided by the ultrasonic transducer array of FIG. 1 can be converted into pixel brightness or color values, such as for presentation on a display in two-dimensions.

In the examples of FIGS. 3A-C, an illustrative example of a presentation of C-scan imaging information can include images 322A-C of a blood vessel 314A-C, such as surrounded by speckle in the region of adjacent tissue 312A-C, such as shown corresponding to planes imaged at various depths (e.g., 6 millimeters (mm), 8 mm, or 10 mm, respectively in FIGS. 3A-C). Generally, the vessel 314A-C can appear blackened or relatively darker (e.g., darker than surrounding tissue) in the constructed images 322A-C, such as surrounded by enhanced borders (e.g., white, or relatively lighter than the vessel interior or surrounding tissue), corresponding to reflection from the interface between the vessel 314A-C wall and surrounding tissue 312A-C. In an example, a blood region of the vessel can include a contrast agent (e.g., DEFINITY®, available from Lantheus Medical Imaging, Inc., Billerica, Mass., U.S.A.). Such a contrast agent can be highly echogenic, such as causing an image of the blood portion of the vessel to appear white or brighter than surrounding tissue. The contrast agent can be administered just before or during scanning, such as to enhance an appearance of one or more vessels to aid the caregiver in locating the desired target vessel via ultrasound imaging.

In an example, a user can provide information about the location of the vessel 314A-C, such as by adjusting a depth of the C-scan imaging plane, such as to obtain the view of FIG. 3B. For example, FIG. 3B image 322B can show a wider separation between the side walls of the vessel 314B as compared to the shallower image 322A of FIG. 3A, or the deeper image 322C of FIG. 3C.

In an example, the user can use an input, such as coupled to a processor circuit and a display, as part of a graphical user interface (GUI), to provide information about the location of the vessel 314B. In an example, the user can provide information about one or more of a center of the vessel 314B, or the location of one or more vessel walls. Such information can be provided via adjusting or moving a graphical indicator over a portion of the image 322B, such as including placing a line or cross-hair along one or more of the vessel walls or along a central axis of the vessel. In an example, a user can indicate a sequence of points or other loci, such as along one or more vessel walls visually identified from the image 322B.

The ultrasound imaging apparatus can then automatically vary the imaging depth so as to provide a C-scan image 322B that can be roughly centered within the vessel. As the transducer array is moved, such as laterally along the surface of the skin, the system can vary the image depth, such as starting from the user-guided depth or using other vessel location information provided by the user, such as to provide or adjust an imaging depth to provide a C-scan image of the vessel that is roughly centered in depth, within the vessel.

In an example, starting from an initial user-guided depth or using other vessel location information, the ultrasound imaging apparatus can automatically scan a range of imaging depths, such as shallower or deeper than the initial depth derived from the user-provided information. In an example, the depth can then be further adjusted (e.g., continuously, or at specified intervals of time, or upon request of the user) as the transducer is moved, or as the relative location of the vessel changes with respect to the transducer (e.g., as the skin is compressed, etc.).

Various techniques can be used to automatically determine the adjusted depth (e.g., to "track" the vessel). For example, one technique for estimating the adjusted depth can include scanning tissue loci corresponding to one or more planes above and below the initial depth. Then, a mean or other central tendency of cross-sectional distance between the vessel 314A-C walls can be determined, such as assigning the adjusted depth to a depth corresponding to a maximum mean cross-sectional distance (or using some other extremum or another central tendency). In an example, a range of depths to be searched can be determined at least in part using information about the vessel diameter or width between the sidewalls, such as provided by the user. In an illustrative example, a 6 mm diameter vessel can use a range of approximately +/−3 mm (or some other range) to constrain the search for the adjusted depth. For example, a warning (audible or visual) can be generated if the center of the vessel cannot be automatically determined within the specified search range.

In an example, one or more feature tracking techniques can be used such as to automatically adjust the depth of the C-scan image, such as using information about the location of one or more vessel 314A-C walls (or information about a change in the location of such vessel 314A-C walls). For example, pixel block matching can be used to determine motion of the one or more vessel 314A-C walls, such as including one or more of a Minimum Sum of Absolute Differences technique, a Maximum Normalized Cross Correlation technique, or a Minimized Sum of Squared Errors technique, such as to determine one or more of an X- or Y-offset in a vessel 314A-C wall location (e.g., in successive scans, such as during a depth search). Generally, such methods are used for detecting a lateral offset in an image plane (e.g., for use in forming a composite of multiple images), however, if the desired features to be tracked are relatively simple or contrast from each other, such techniques might still be used. In an example, one or more motion estimates of one or more features can be post-processed. For example, a motion estimate of a feature included in the imaging information can be low-pass filtered or median filtered, such as to reduce or minimize the impact of outliers or noise.

For example, as the vessel wall separation increases or decreases (e.g., as the C-scan imaging plane is automatically varied during a search for the adjusted plane depth), such an increase or decrease can be used to provide feedback. For example, if the vessel wall separation is decreasing, the direction of the search (e.g., shallower or deeper) can be reversed or otherwise adjusted.

While the term "pixel" is used, such feature tracking techniques need not be restricted to operating on a (re) constructed C-scan image itself. For example, such techniques can include using one or more other forms of raw or intermediate ultrasound imaging data or information, such as beamformed transducer information (e.g., RF data, such as delayed, or complex-sampled and phase-rotated), video information (e.g., video B-mode information), a tissue harmonic signal arising from non-linear propagation, Doppler information (e.g., velocity information), other motion information obtained via non-Doppler techniques (e.g., decorrelation analysis).

In an example, blood motion or velocity information can be used to assist in automatically determining the adjusted depth. For example, the center of the long axis of the vessel can correspond to a location where blood motion is maximized, or where the velocity information indicates a velocity maximum (e.g., from the motion of blood through the vessel). In an example, velocity information can be obtained using one or more techniques or apparatus mentioned in Pang, et al., U.S. Pat. No. 6,190,321, "Medical Diagnostic Ultrasound Imaging Methods for Estimating Motion between Composite Ultrasonic Images and Recovering Color Doppler Values from Composite Images," which is hereby incorporated by reference herein in its entirety, including its disclosure of using Doppler-mode ultrasonic techniques to extract velocity information, or Kasai, et al., "Real-Time Two-Dimensional Blood Flow Imaging Using an Autocorrelation Technique," IEEE Transactions on Sonics and Ultrasonics, Vol. SU-32, No. 3, May 1985, which is also hereby incorporated by reference herein in its entirety.

In an example, one or more indicators can be presented to indicate a present or adjusted C-scan imaging depth, such as an alphanumeric indicator, overlaying or otherwise comprising a portion of the constructed image 322A-C, or a line aligned with or overlaying the constructed image 322A-C. For example, in FIGS. 3A-C, a depth indicator 324A-C can include a bar graph display, such as including a scale and one or more alphanumeric indicators, such as a filled or unfilled block within rectangle whose height (or width, if rotated) is indicative of a maximum range of imaging depths. In an example, an indication can be provided, such as audibly or via the display, to the user, such as in response to a deviation in estimated depth above a specified threshold (or outside a specified range), or when confidence in the estimator is becoming unreliable, such as indicated by one or more "quality of tracking" metrics provided by a feature tracking or pixel block matching technique of the examples discussed above.

In an example, such as during either an automatic determination of the adjusted depth, or in relation to construction of an image for presentation to a user, one or more techniques can be used to suppress or remove noise or speckle. For example, noise or speckle (e.g., in the tissue 312A-C adjacent to the vessel 314A-C in images 322A-C) can be suppressed at least in part by low pass filtering, median filtering, anisotropic diffusion, or using one or more other techniques. In the case of speckle in particular, spatial or frequency compounding can be used, in which de-correlated or independent speckle patterns can be averaged. Generally, compounding can include using different sub-apertures to obtain at least approximately independent speckle patterns or using imaging planes that can be slightly offset in depth from each other. In an illustrative example for C-scan imaging, speckle patterns can be obtained from successive acquisitions, such as at −1 mm, 0 mm, and +1 mm with respect to the desired imaging plane (either for display or depth search). In such an illustrative example, the speckle pattern generally changes significantly while the underlying anatomy remains roughly static, allowing the speckle to be at least partially suppressed (e.g., by averaging).

FIG. 4 illustrates generally an illustrative example 400 of side-by-side imaging information including both B-scan and C-scan ultrasound imaging information including a portion of a vessel, such as for graphical presentation to a user. While the examples of FIGS. 1, 2, and 3A-C generally refer to C-scan imaging in a plane parallel to the transducer array surface, it is possible to use such C-scan image information to construct a "synthetic" B-scan image corresponding to a desired plane perpendicular to the surface of the ultrasound transducer array. For example, in FIG. 4, a variety of depths can be automatically scanned, such as using the apparatus of FIG. 1, such as to construct a B-scan image 424, including an elevation cross-sectional view of a vessel 414A surrounded by tissue 412A. Various planes can cut through the B-scan view, such as a first plane 420A, corresponding to loci within tissue 412A that can be shown longitudinally in the plan view of an adjacent C-scan image 422, showing tissue 412B and a long axis of the vessel 414B. The separation between the vessel 414B walls in C-scan image can correspond to the distance between the vessel 414A walls in the plane 420A. In an example, the user can provide a corrected depth to initially guide the search for a subsequent adjusted C-scan imaging depth, such as by moving an overlay on the synthetic B-scan image 424 indicative of the plane 420A to the location of the center of the vessel cross-section as shown in a plane 420B. Such an overlay, feature, or other indication can include a cross-hair, or one or more other indicia, such as discussed below in the examples of FIGS. 5A-C. In an example, the B-scan image 424 can be displayed instead of the C-scan image 422, or the user can toggle between the images, or both images can be displayed on a commonly-shared display, etc., such as according to a user preference or the user input.

Synthetic B-scan information need not be used to construct an image for presentation to the user. For example, synthetic B-scan imaging information (or other data or information corresponding to a plane perpendicular to the surface of the transducer array) can be used to provide an adjusted C-scan imaging depth. For example, as discussed above, pixel block matching, shape tracking, or other feature tracking can be used to automatically identify the location of the center of the roughly circular cross-section of the vessel 414A as shown in the synthetic B-scan image 424. In the case of a bifurcation of the vessel, such tracking can include attempting to track the larger-diameter vessel extending away from the bifurcation, or can include generating an alarm or other alert if the level of confidence in identifying the vessel cross-section falls below a specified threshold.

FIGS. 5A-C illustrate generally an illustrative example that can include a repositionable or resizable indicator that can be manipulated by a user, such as to provide positional information about a vessel to an ultrasound imaging apparatus, such as including information about a depth of a vessel. The images 524A-C can include synthetic B-scan images provided to a user as a portion of a graphical user interface (GUI) to assist the user in identifying an initial depth of the vessel. In the example of FIG. 5A, the indicator 520A is shown as a circle, but such an indicator need not be circular. The indicator 520A can be repositioned to the center of the vessel 514A. In FIG. 5B, the indicator 520B can be resized, such as to provide the ultrasonic imaging apparatus with an estimate of both the depth of the center of the vessel 514B, along with a diameter or separation between the sidewalls at the center of the vessel 514B. In FIG. 5C, the indicator 520C, after adjustment by the user, can overlay the vessel 514C.

Figure 6A:
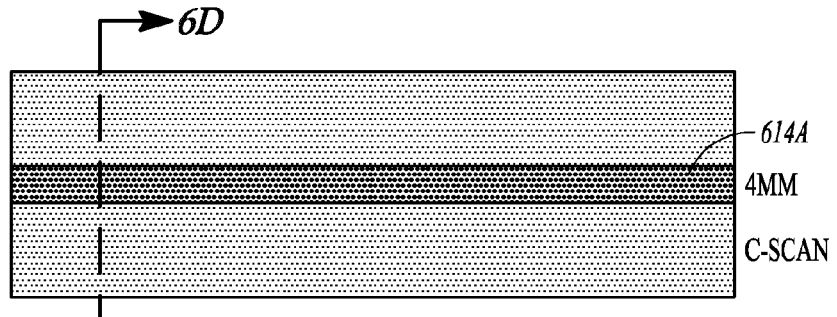
FIGS. 6A-D illustrate generally illustrative examples of ultrasound imaging information that can include C-scan ultrasound imaging information showing a boundary of a vessel, along with corresponding indicators of depth overlaid on B-scan ultrasound imaging information including a cross-section of the vessel.
Figure 6B:
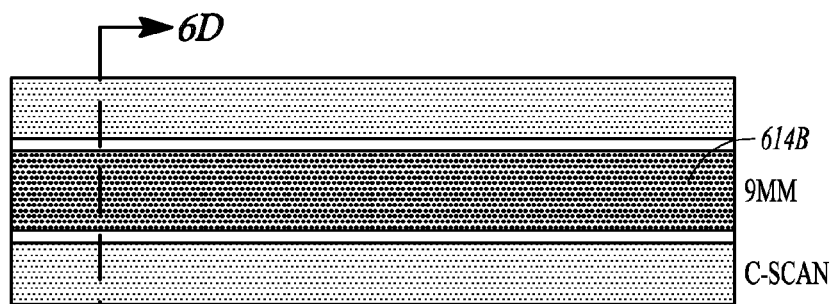
Figure 6C:
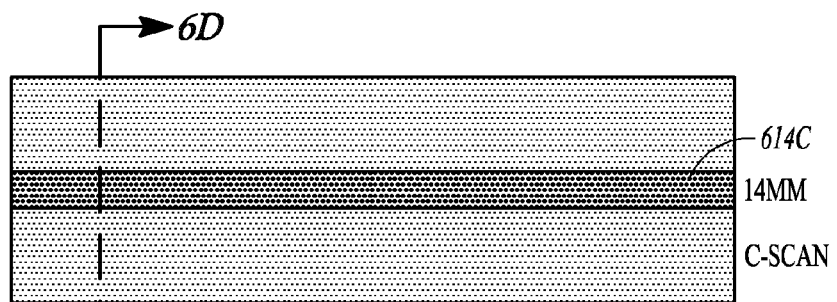
Figure 6D:
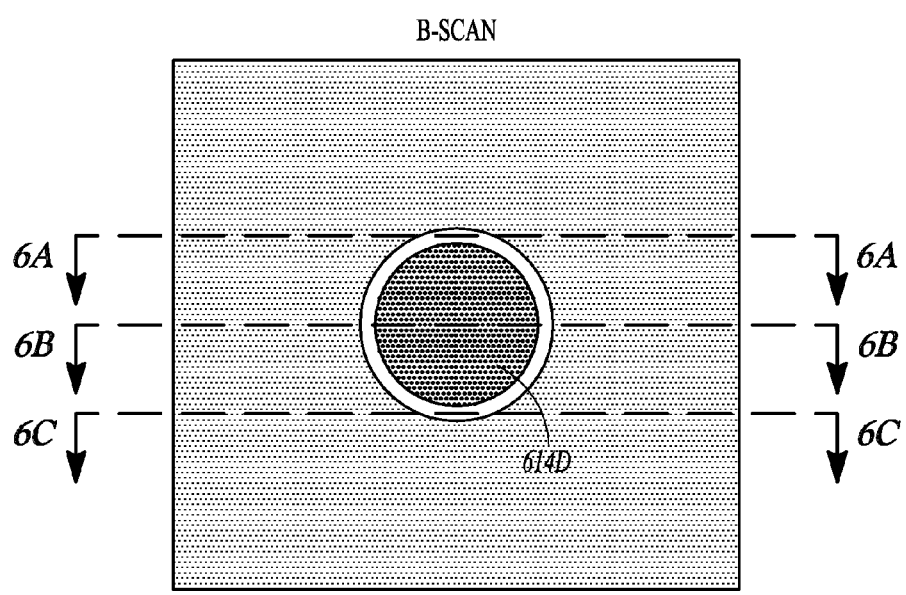

FIGS. 6A-D illustrate generally illustrative examples of ultrasound imaging information that can include C-scan ultrasound imaging information showing a boundary of a vessel, along with corresponding indicators of depth overlaid on B-scan ultrasound imaging information including a cross-section of the vessel. As discussed in the examples above, a separation between sidewalls of the vessel can be used as one parameter to aid in automatically determining an adjusted depth for C-scan imaging. FIGS. 6A-D illustrate generally another approach that can be used. In FIGS. 6A-D, a vessel 614A-D can include an interface (e.g., the vessel wall) between the tissue 614A-D and the vessel interior that is highly reflective of ultrasonic energy. Such reflection can be almost specular, such as providing a highly enhanced (e.g., white, or relatively lighter than the surrounding tissue) representation in a corresponding reconstructed image. Thus, in an example, a variety of C-scan depths can be evaluated, such as to identify the top of the vessel (e.g., as shown in the plane of the vessel 614A of FIG. 6A), and the bottom of the vessel (e.g., as shown in the plane of the vessel 614C of FIG. 6C), such as using pixel block matching or feature tracking techniques to identify highly enhanced ultrasonic signature of the vessel 614A-D wall. In an example, once the depth of the top of the vessel 614A and the bottom of the vessel 614C have been determined, a mid-point (or other location) between the two depths can be used to estimate a depth of the center of the vessel (e.g., as shown in the plane of the vessel 614B in FIG. 6B). In FIG. 6D, a cross-section (e.g., B-scan projection) view is shown to illustrate the locations of the planes of the C-scan projections of FIGS. 6A-C with respect to the vessel 614D cross-section of FIG. 6D.

Figure 7:
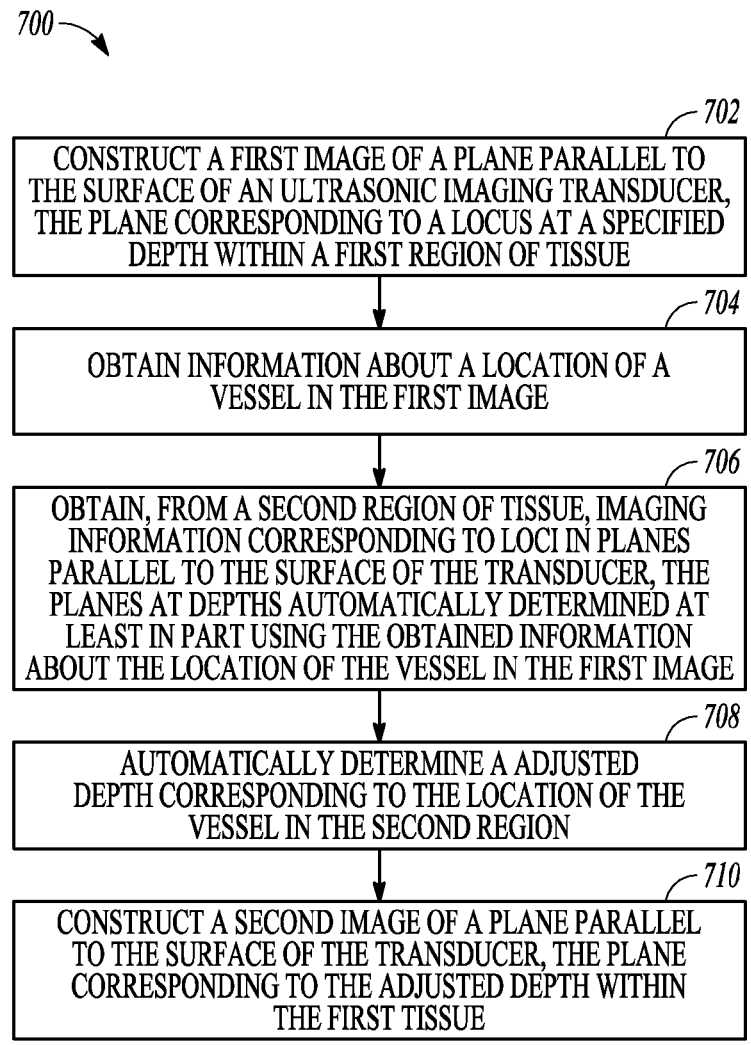
FIG. 7 illustrates generally an example of a technique that can include constructing an image of a region of tissue, such as using an adjusted depth determined automatically by an ultrasound imaging apparatus.

FIG. 7 illustrates generally an example of a technique 700 that can include constructing an image of a region of tissue, such as using an adjusted depth determined automatically by an ultrasound imaging apparatus. At 702, the technique 700 can include constructing a first image of a plane parallel to the surface of an ultrasonic transducer array (e.g., a C-scan image), such as corresponding to a locus within the tissue at a specified depth from the transducer. At 704, the technique 700 can include obtaining information about a location of a vessel in the first image, such as using one or more techniques or apparatus as discussed in the examples above. For example, the obtaining of information can include using information obtained from a user (e.g., an initial vessel depth, a separation between sidewalls of the vessel, etc.), or the information can be determined automatically such as by searching for a dark feature, a bright feature, or other information indicative of a vessel.

At 706, the technique 700 can include obtaining, from a second region of tissue, imaging information corresponding to loci in planes parallel to the surface of the transducer, the planes at depths automatically determined at least in part using the obtained information about the location of the vessel in the first image. Such depths can include a search performed by ultrasonic imaging apparatus to identify the depth of a center of a long axis of the vessel in the second tissue region, because the vessel depth can vary as the transducer is moved from a location above the first region, to a location above the second region, along the skin. At 708, the technique 700 can include automatically determining an adjusted depth corresponding to the location of the vessel in the second region. At 710, the technique 700 can include constructing a second image of a plane parallel to the surface of the transducer, the plane corresponding to the adjusted depth within the tissue. In an example, the technique 700 can include using one or more of the apparatus or techniques described in the examples above, such as to aid a user (e.g., a caregiver) in locating a target vessel amongst other vessels, for a needle insertion procedures, such as using an external C-scan ultrasonic imaging apparatus.

In an example, such as in relation to one or more of the apparatus or techniques discussed above in FIG. 1, 2, 3A-C, 4, 5A-C, 6A-D, 7, or 8A-B, the area of imaging information used for estimation or determination of the adjusted depth for successive C-scan images can be constrained to a region within a specified absolute range of depths, or within a range of depths specified in relation to an initial specified depth. In an example (either involving C-scan, or B-scan information), the computation domain for feature tracking can be restricted to a spatial (or temporal) information corresponding to the region within or nearby the cross section of the vessel being targeted, such as to reduce computation burden.

Figure 8A:
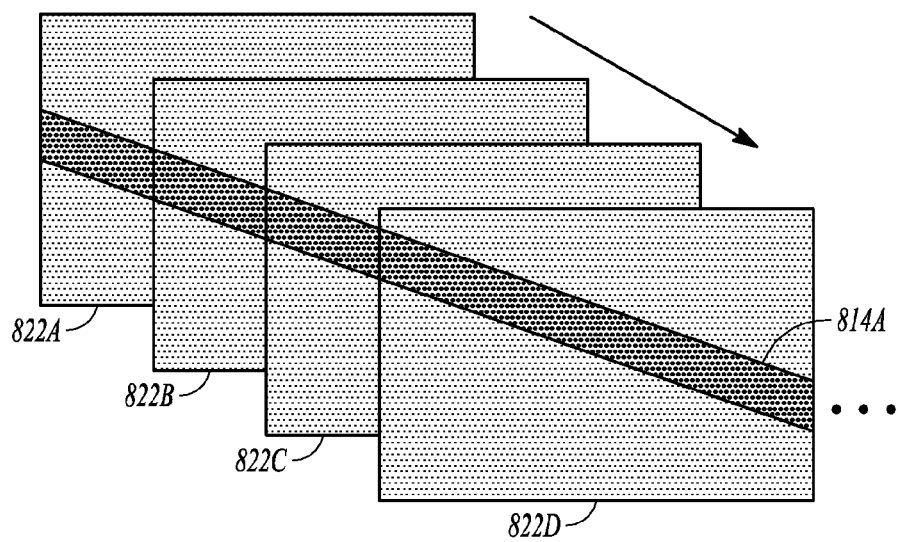
FIGS. 8A-B illustrate generally an illustrative example of combining imaging information from individual scans into a composite image.
Figure 8B:
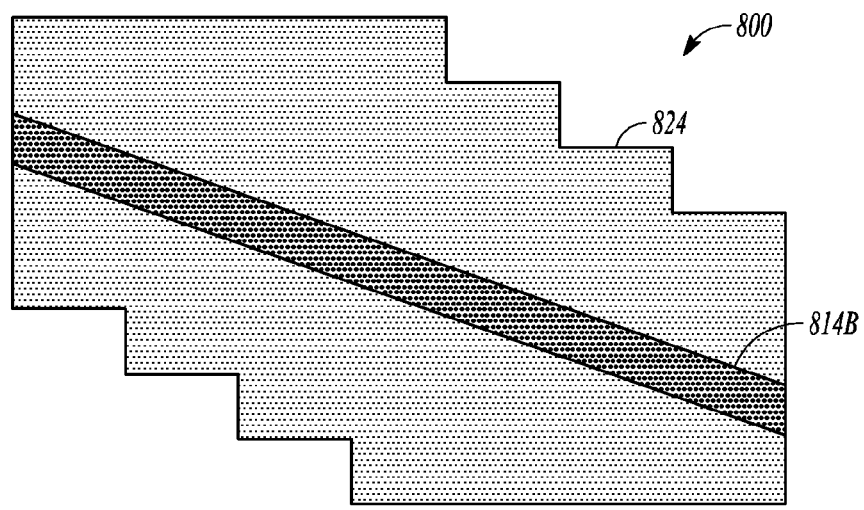

FIGS. 8A-B illustrate generally an illustrative example of combining imaging information from individual scans into a composite image 824, such as in relation to one or more of the apparatus or techniques discussed above in FIG. 1, 2, 3A-C, 4, 5A-C, 6A-D, or 7. One or more techniques can be used to provide a composite or "mosaic" of multiple constructed images, such as one or more images including information from more than one tissue region. For example, in the illustrative example of FIG. 8A, C-scan imaging information can be obtained such as corresponding to a field of view in a first location 822A, a second location 822B, a third location 822C, a fourth location 822D, etc., as a transducer array is moved along the surface of a subject. One or more portions of an underlying vessel 814A can be captured in the various fields corresponding to the locations 822A-D, such as including an adjusted depth to provide imaging information centered with respect to a central axis of the vessel 814A. Then, such as in the illustrative example 800 of FIG. 8B, a mosaic or combined image having an extended field of view can be constructed, such as including a rendering of a vessel 814B, corresponding to imaged portions of the vessel 814A in one or more of the locations 822A-D. Such a mosaic or composite can provide a field of view that can be larger than the field of view provided by an image reconstructed from a single tissue region, such as imaged at a single depth using a C-scan imaging mode.

For example, the apparatus of FIG. 1 can be used to continuously or periodically update the adjusted depth of the vessel (e.g., tracking the depth of the vessel), and either a two-dimensional or three-dimensional representation of the vessel can be presented. For example, speckle or pixel block matching techniques can be used to align and stitch segments or portions of the vessel from separate scans into a composite image, similar to the techniques discussed above with respect to feature tracking in the examples of FIGS. 3A-C. In an example, a lateral offset between successive scan images (e.g., corresponding to different tissue regions) can be determined using such speckle or pixel block matching techniques. In an example, such pixel block matching or feature tracking techniques can include one or more techniques mentioned in Weng, et. al., U.S. Pat. No. 5,575,286, "Method and apparatus for generating large compound ultrasound image," which is hereby incorporated herein by reference in its entirety, including its disclosure of techniques for partitioning ultrasound information into pixel blocks and analyzing such blocks in order to construct a compound image having an extended field of view.

A composite representation can generally be displayed as an elongated vessel representation, visualized in either two or three dimensions. In the case of a two-dimensional representation, depth information can still be presented such as using one or more indicia overlaying or aligned with the representation of the vessel, the one or more indicia indicating a depth of the vessel at one or more locations corresponding to the one or more indicia. In an example, a color of the vessel at various loci along the representation of the vessel can be used to indicate the relative depth of the vessel in relation to the surface of the transducer, for vessel presentation in either two dimensions (e.g., "flattened") or in a three-dimensional view. A color bar or "temperature bar" can be provided, such as providing the user with a mapping between a particular color and a particular depth.

In an example, a three-dimensional representation of a composite of the imaging information can be constructed such as using one or more feature tracking or motion estimation techniques mentioned in Hossack, et al., U.S. Pat. No. 6,014,473, "Multiple Ultrasound Image Registration System, Method, and Transducer," which is herein incorporated by reference in its entirety.

In an example, dynamic Doppler information from multiple scanned image fields can be combined, such as to provide an extended field of view that can include both spatial and temporal extension, such as to provide information about dynamic (e.g., pulsatile flow) for presentation to the user. Such a composite can be determined using apparatus or techniques, such as mentioned in Pang, et al., U.S. Pat. No. 6,558,325, "Medical diagnostic ultrasonic imaging method and system for displaying multi-phase, multi-frame images," which is hereby incorporated herein by reference in its entirety.

One or more techniques, such as mentioned in Pang '321, or Pang '325, can be used, such as to construct an image for presentation to a user, the image including one or more of gray C-scan information or "color" Doppler information (e.g., indicative of blood flow or other dynamic information). For example, Doppler or other motion information can be used to construct a colorized representation of motion within one or more tracked blood vessels. Such color information can be coded or presented according to a variety of techniques, such as displaying a portion of a vessel in color when motion or velocity information corresponding to the portion exceeds a specified threshold. In an example, a range of colors can be mapped to motion or velocity, such as a scalar (e.g., unsigned) velocity or motion magnitude, or a vector (e.g., signed) representation (e.g., blood flow in one direction represented by a blue hue, blood flow in the opposite direction represented by a red hue, etc.).

In an example, apparatus or techniques such as discussed in the examples above can be used to construct a composite image or mosaic without requiring that the depth of the vessel be automatically tracked. For example, the techniques discussed above can be generally applicable to constructing a mosaic of C-scan imaging information, regardless of whether such information includes scans that have been automatically depth-adjusted.

In an example, such as in relation to one or more of the apparatus or techniques discussed above in FIG. 1, 2, 3A-C, 4, 5A-C, 6A-D, 7, or 8A-B, an audible or visual indicator or warning can be provided to the user such as when one or more metrics indicative of the confidence of the adjusted depth exceed or drop below a specified threshold or violate a specified range. For example, during automatic tracking of vessel depth, if an estimate of an adjusted depth for use in constructing an image deviates from a previous determination or deviates from the user-supplied initial depth by more than a specified amount, a warning can be displayed or an alarm can be sounded. In an example, a color or other overlay can be adjusted such as to indicate a loss of confidence in the depth estimate.

For example, one such "quality of estimate" metric can include determining a ratio or other relative indication of a minimum sum of absolute differences relative to a mean sum of absolute differences for all calculated sums during a particular depth estimation (or aggregated across multiple estimates). In this illustrative example, a lower ratio indicates a better estimate, and accordingly a threshold can be specified above which an alarm or warning can be generated.

In an example, the initial depth estimate need not be provided by a user, but can be obtained automatically, such as using one or more of the apparatus or techniques discussed above in relation to automatically adjusting the depth of the scan. For example, an initial search can be performed automatically, such as to determine a location of a dark area or using the bright reflections of vessel walls to determine an initial depth. In the case of synthetic B-scan image information, shape tracking or one or more other techniques can be used, such as to initially identify a approximately circular cross section of a likely vessel target, including automatically determining one or more of a diameter or a central axis location of the vessel.

VARIOUS EXAMPLES AND NOTES

Example 1 can include, or can optionally be combined with subject matter of one or any combination of Examples 19-35 to include, subject matter (such as a method, a means for performing acts, or a machine-readable medium including instructions that, when performed by the machine, can the machine to perform acts) comprising constructing a first image of a plane parallel to the surface of an ultrasonic imaging transducer, the plane corresponding to a locus at a specified depth within a first region of tissue, using information obtained from the imaging transducer, obtaining information about a location of a vessel in the first image, obtaining, from a second region of tissue, imaging information corresponding to loci in planes parallel to the surface of the transducer, the planes at depths automatically determined at least in part using the obtained information about the location of the vessel in the first image, automatically determining an adjusted depth corresponding to the location of the vessel in the second region, and constructing a second image of a plane parallel to the surface of the transducer, the plane corresponding to the adjusted depth within the tissue, the first and second regions offset from each other.

In Example 2, the subject matter of Example 1 can optionally include constructing the first image including insonifying the first region of tissue using the ultrasonic transducer array, and in response to the insonification, obtaining echo information from the insonified first region of tissue, and obtaining imaging information from the second region of the tissue including insonifying the second region of tissue and obtain echo information from the insonified second region of tissue, the echo information corresponding to loci in planes parallel to the surface of the transducer, the planes at depths automatically determined at least in part using the obtained information about the location of the vessel in the first image.

In Example 3, the subject matter of one or more any combination of Examples 1-2 can optionally include a specified depth corresponding to the first image including information obtained via a user input.

In Example 4, the subject matter of one or more any combination of Examples 1-3 can optionally include obtaining information about a location of a vessel in the first image including obtaining information about one or more of a vessel center, or a location of the vessel walls, via a user input.

In Example 5, the subject matter of one or more any combination of Examples 1-4 can optionally include information obtained via the user input comprising one or more of a selection made via a keyboard, a mouse, a rotary control input, a touch-screen input, or a soft-key input located on or near a display.

In Example 6, the subject matter of one or more any combination of Examples 1-5 can optionally include automatically determining an adjusted depth corresponding to the location of the vessel in the second region including determine a mean cross-sectional distance between the vessel walls corresponding to each of the scanned planes in the second region of tissue using an initial depth determined at least in part using the information about the vessel location obtained via the user input, estimating a depth corresponding to a maximum mean cross-sectional distance using the determined mean cross-sectional distances, and assigning the estimated depth as the adjusted depth.

In Example 7, the subject matter of one or more any combination of Examples 1-6 can optionally include automatically determining an adjusted depth corresponding to the location of the vessel in the second region including determining a first depth using obtained imaging information indicative of a shallow boundary of the vessel, closer to the imaging transducer in depth than a deep boundary of the vessel, determining a second depth indicative of the deep boundary of the vessel, estimating a depth corresponding to the center of the long axis of the vessel between the shallow and deep boundaries, assigning the estimated depth as the adjusted depth, and one or more of the determining the first depth or determining the second depth including using information about the vessel location obtained via the user input.

In Example 8, the subject matter of one or more any combination of Examples 1-7 can optionally include determining the depths of one or more of the shallow or deep boundaries of the vessel including iteratively obtaining imaging information, and constructing images, corresponding to a variety of depths, until a bright reflection corresponding to an interface between the vessel and the surrounding tissue is detected.

In Example 9, the subject matter of one or more any combination of Examples 1-8 can optionally include declare an error if no bright reflection corresponding to an interface between the vessel and the surrounding tissue can be detected.

In Example 10, the subject matter of one or more any combination of Examples 1-9 can optionally include automatically determining an adjusted depth corresponding to the location of the vessel in the second region including obtaining imaging information including blood motion information, estimating a depth corresponding to the center of the long axis of the vessel where the blood motion information indicates a maximum blood motion, assigning the estimated depth as the adjusted depth, the estimating a depth corresponding to the center of the long axis of the vessel, including using information about the vessel location obtained via the user input.

In Example 11, the subject matter of one or more any combination of Examples 1-10 can optionally include presenting the constructed second image via a display.

In Example 12, the subject matter of one or more any combination of Examples 1-11 can optionally include displaying an indicator of the adjusted depth on or near the constructed second image via the display, the indicator including one or more of a bar-graph, an alphanumeric indicator, a color overlaying or otherwise comprising a portion of the constructed second image, or a line aligned with or overlaying the constructed second image.

In Example 13, the subject matter of one or more any combination of Examples 1-12 can optionally include obtaining imaging information including blood motion information, constructing a composite image including the vessel and a representation of blood motion corresponding to at least a portion of the vessel, and presenting the constructed image via the display.

In Example 14, the subject matter of one or more any combination of Examples 1-13 can optionally include constructing a third image of a plane perpendicular to the surface of the imaging transducer, the third image including a cross-sectional view of the vessel, the third image determined using information about a series of constructed images corresponding various depths of planes parallel to the surface of the imaging transducer.

In Example 15, the subject matter of one or more any combination of Examples 1-14 can optionally include constructing a composite image including the first and second constructed images.

In Example 16, the subject matter of one or more any combination of Examples 1-15 can optionally include constructing a composite image including constructing a three-dimensional representation of the vessel.

In Example 17, the subject matter of one or more any combination of Examples 1-16 can optionally include constructing a composite image including constructing a two-dimensional representation of the vessel, including one or more indicia overlaying or aligned with the representation of the vessel, the one or more indicia indicating a depth of the vessel at one or more locations corresponding to the one or more indicia.

In Example 18, the subject matter of one or more any combination of Examples 1-17 can optionally include first and second regions that can at least partially overlap with each other.

Example 19 includes subject matter (such as an apparatus) comprising an ultrasonic imaging transducer configured to obtain imaging information from tissue, and a processor circuit coupled to the imaging transducer and configured to construct a first image of a plane parallel to the surface of the imaging transducer, the plane corresponding to a locus at a specified depth within a first region of tissue, using information obtained from the imaging transducer, obtain information about a location of a vessel in the first image, obtain, from a second region of tissue, imaging information corresponding to loci in planes parallel to the surface of the transducer, the planes at depths automatically determined at least in part using the obtained information about the location of the vessel in the first image, automatically determine an adjusted depth corresponding to the location of the vessel in the second region, and construct a second image of a plane parallel to the surface of the imaging transducer, the plane corresponding to the adjusted depth within the tissue, the first and second regions offset from each other.

In Example 20, the subject matter of Example 19 can optionally include an ultrasonic transducer array located externally to the tissue, the processor circuit configured to construct the first image configured to control the ultrasonic transducer array to insonify the first region of tissue using the ultrasonic transducer array, and in response to insonification, obtain echo information from the insonified first region of tissue, and the processor circuit configured to obtain imaging information from the second region of tissue configured to control the ultrasonic transducer array to insonify the second region of tissue and obtain echo information from the insonified second region of tissue, the echo information corresponding to loci in planes parallel to the surface of the transducer, the planes at depths automatically determined at least in part using the received information about the location of the vessel in the first image.

In Example 21, the subject matter of one or more any combination of Examples 19-20 can optionally include a user input, and the specified depth corresponding to the first image includes information obtained by the user input.

In Example 22, the subject matter of one or more any combination of Examples 19-21 can optionally include a user input, the information about the location of the vessel image includes information obtained by the user input about one or more of a vessel center, or a location of the vessel walls.

In Example 23, the subject matter of one or more any combination of Examples 19-22 can optionally include a user input comprising one or more of a keyboard, a mouse, a rotary control input, a touch-screen input, or a soft-key input located on or near a display.

In Example 24, the subject matter of one or more any combination of Examples 19-23 can optionally include a processor circuit configured to automatically determine an adjusted depth, the processor circuit configured to determine a mean cross-sectional distance between the vessel walls corresponding to each of the scanned planes in the second region of tissue using an initial depth determined at least in part using the information about the vessel location obtained using the user input, estimate a depth corresponding to a maximum mean cross-sectional distance using the determined mean cross-sectional distances, and assign the estimated depth as the adjusted depth.

In Example 25, the subject matter of one or more any combination of Examples 19-24 can optionally include a processor circuit configured to automatically determine an adjusted depth, the processor circuit configured to determine a first depth using obtained imaging information indicative of a shallow boundary of the vessel, closer to the imaging transducer in depth than a deep boundary of the vessel, determine a second depth indicative of the deep boundary of the vessel, estimate a depth corresponding to the center of the long axis of the vessel between the shallow and deep boundaries, and assign the estimated depth as the adjusted depth, the one or more of the determining the first depth or determining the second depth includes using information about the vessel location obtained via the user input.

In Example 26, the subject matter of one or more any combination of Examples 19-25 can optionally include a processor circuit configured to obtain imaging information including blood motion information, estimate a depth corresponding to the center of the long axis of the vessel where the blood motion information indicates a maximum blood motion, and assign the estimated depth as the adjusted depth, the estimating a depth corresponding to the center of the long axis of the vessel includes using information about the vessel location obtained using the user input.

In Example 27, the subject matter of one or more any combination of Examples 19-26 can optionally include a display coupled to the processor circuit, and the processor circuit is configured to present the constructed second image using the display.

In Example 28, the subject matter of one or more any combination of Examples 19-27 can optionally include a processor circuit configured to present an indicator of the adjusted depth on or near the constructed second image using the display, the indicator including one or more of a bar-graph, an alphanumeric indicator, a color overlaying or otherwise comprising a portion of the constructed second image, or a line aligned with or overlaying the constructed second image.

In Example 29, the subject matter of one or more any combination of Examples 19-28 can optionally include a processor circuit configured to obtain imaging information including blood motion information, construct a composite image including the vessel and a representation of blood motion corresponding to at least a portion of the vessel, and present the constructed image via the display.

In Example 30, the subject matter of one or more any combination of Examples 19-29 can optionally include a processor circuit is configured to construct a third image of a plane perpendicular to the surface of the imaging transducer, the third image including a cross-sectional view of the vessel, the third image determined using information about a series of constructed images corresponding various depths of planes parallel to the imaging transducer, and present the third image using the display.

In Example 31, the subject matter of one or more any combination of Examples 19-30 can optionally include a processor circuit configured to construct a composite image including the first and second constructed images, and present the composite image using the display.

In Example 32, the subject matter of one or more any combination of Examples 19-31 can optionally include a processor circuit configured to construct a three-dimensional representation of the vessel, and to present the three-dimensional representation of the vessel using the display.

In Example 33, the subject matter of one or more any combination of Examples 19-32 can optionally include a processor circuit configured to construct a two-dimensional representation of the vessel and present the two-dimensional representation of the vessel using the display, the presentation including one or more indicia overlaying or aligned with the representation of the vessel, the one or more indicia indicating a depth of the vessel at one or more locations corresponding to the one or more indicia.

In Example 34, the subject matter of one or more any combination of Examples 19-33 can optionally include first and second regions that can at least partially overlap with each other.

Example 35 includes subject matter (such as an apparatus) comprising a user input, a display, an ultrasonic imaging transducer configured to obtain imaging information from tissue, and a processor circuit coupled to the ultrasonic transducer array and configured to construct a first image of a plane parallel to the surface of the imaging transducer, the plane corresponding to a locus at a specified depth within the first region of tissue, using information obtained from the imaging transducer, present the constructed first image using the display, obtain information about a location of a vessel in the first image using the user input, obtain, from a second region of tissue, imaging information corresponding to loci in planes parallel to the surface of the transducer, the planes at depths automatically determined at least in part using the obtained information about the location of the vessel in the first image, automatically determine an adjusted depth corresponding to the location of the vessel in the second image, construct a second image of a plane parallel to the surface of the imaging transducer, the plane corresponding to the adjusted depth within the tissue, and present the constructed second image using the display, the first and second regions offset from each other.

In Example 36, the subject matter of one or more any combination of Examples 19-35 can optionally include an imaging transducer comprising an ultrasonic transducer array located externally to the tissue, the processor circuit configured to construct the first image is configured to control the ultrasonic transducer array to insonify the first region of tissue using the ultrasonic transducer array, and in response to insonification, obtain echo information from the insonified first region of tissue, and the processor circuit configured to obtain imaging information from the second region of tissue, the processor circuit configured to control the ultrasonic transducer array to insonify the second region of tissue and obtain echo information from the insonified second region of tissue, the echo information corresponding to loci in planes parallel to the surface of the transducer, the planes at depths automatically determined at least in part using the received information about the location of the vessel in the first image.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A non-transitory processor-readable medium comprising instructions that, when performed by the processor, cause the processor to:
    construct a first image of a plane parallel to the surface of an ultrasonic imaging transducer, the plane corresponding to a locus at a specified depth within a first region of tissue, using information obtained from the imaging transducer;
    obtain information about a location of a vessel in the first image;
    obtain, from a second region of tissue, imaging information corresponding to loci in planes parallel to the surface of the transducer, the planes at depths automatically determined at least in part using the obtained information about the location of the vessel in the first image;
    automatically determine an adjusted depth corresponding to the location of the vessel in the second region including:
        determining a first depth using obtained imaging information indicative of a shallow boundary of the vessel, closer to the imaging transducer in depth than a deep boundary of the vessel;
        determining a second depth indicative of the deep boundary of the vessel;
        estimating a depth corresponding to the center of the vessel between the shallow and deep boundaries; and
        assigning the estimated depth as the adjusted depth; and
    construct a second image of a plane parallel to the surface of the transducer, the plane corresponding to the adjusted depth within the tissue;
    wherein the first and second regions are offset from each other.

2. The non-transitory processor-readable medium of claim 1, wherein the imaging transducer comprises an ultrasonic transducer array located externally to the tissue; wherein the instructions to construct the first image comprise instructions that cause the processor to:
    insonify the first region of tissue using the ultrasonic transducer array; and
    in response to the insonification, obtain echo information from the insonified first region of tissue; and
    wherein the instructions to obtain imaging information from the second region of the tissue include instructions that cause the processor to:
        insonify the second region of tissue and obtain echo information from the insonified second region of tissue, the echo information corresponding to loci in planes parallel to the surface of the transducer, the planes at depths automatically determined at least in part using the obtained information about the location of the vessel in the first image.

3. The non-transitory processor-readable medium of claim 1, wherein the specified depth corresponding to the first image includes information obtained via a user input.

4. The non-transitory processor readable medium of claim 1, wherein the instructions to automatically determine an adjusted depth corresponding to the location of the vessel in the second region include instructions to obtain imaging information including blood motion information;
    estimate a depth corresponding to the center of the long axis of the vessel where the blood motion information indicates a maximum blood motion; and
    assign the estimated depth as the adjusted depth.

5. The non-transitory processor-readable medium of claim 1, wherein the first and second regions at least partially overlap with each other.

6. The non-transitory processor-readable medium of claim 1, wherein the instructions that cause the processor to obtain information about a location of a vessel in the first image include instructions that cause the processor to obtain information about one or more of a vessel center, or a location of the vessel walls, via a user input.

7. The non-transitory processor-readable medium of claim 6, wherein the information obtained via the user input includes one or more of a selection made via a keyboard, a mouse, a rotary control input, a touch-screen input, or a soft-key input located on or near a display.

8. The non-transitory processor-readable medium of claim 6, wherein the instructions to automatically determine an adjusted depth corresponding to the location of the vessel in the second region include instructions to:
    determine mean cross-sectional distances between the vessel walls corresponding to each of the scanned planes in the second region of tissue using an initial depth determined at least in part using the information about the vessel location obtained via the user input;
    estimate a depth corresponding to a maximum mean cross-sectional distance using the determined mean cross-sectional distances; and
    assign the estimated depth as the adjusted depth.

9. The non-transitory processor-readable medium of claim 6, wherein one or more of the determining the first depth or determining the second depth includes using information about the vessel location obtained via the user input.

10. The non-transitory processor-readable medium of claim 1, wherein the instructions to determine the depths of one or more of the shallow or deep boundaries of the vessel include instructions to iteratively obtain imaging information, and construct images, corresponding to a variety of depths, until a bright reflection corresponding to an interface between the vessel and the surrounding tissue is detected.

11. The non-transitory processor-readable medium of claim 10, wherein the instruction comprise instructions that cause the processor to declare an error if no bright reflection corresponding to an interface between the vessel and the surrounding tissue can be detected.

12. The non-transitory processor-readable medium of claim 1, wherein the instructions comprise instructions that cause the processor to present the constructed second image via a display.

13. The non-transitory processor-readable medium of claim 12, wherein the instructions comprise instructions that cause the processor to display an indicator of the adjusted depth on or near the constructed second image via the display, the indicator including one or more of a bar-graph, an alphanumeric indicator, a color overlaying or otherwise comprising a portion of the constructed second image, or a line aligned with or overlaying the constructed second image.

14. The non-transitory processor-readable medium of claim 12, wherein the instructions comprise instructions that cause the processor to:
obtain imaging information including blood motion information;
construct a composite image including the vessel and a representation of blood motion corresponding to at least a portion of the vessel; and
present the constructed image via the display.

15. The non-transitory processor-readable medium of claim 12, wherein the instructions comprise instructions to construct a third image of a plane perpendicular to the surface of the imaging transducer, the third image including a cross-sectional view of the vessel, the third image determined using information about a series of constructed images corresponding to various depths of planes parallel to the surface of the imaging transducer.

16. The non-transitory processor-readable medium of claim 1, wherein the instructions comprise instructions to construct a composite image including the first and second constructed images.

17. The non-transitory processor-readable medium of claim 16, wherein the instructions to construct the composite image include instructions to construct a three-dimensional representation of the vessel.

18. The non-transitory processor-readable medium of claim 16, wherein the instructions to construct the composite image include instructions to construct a two-dimensional representation of the vessel, including one or more indicia overlaying or aligned with the representation of the vessel, the one or more indicia indicating a depth of the vessel at one or more locations corresponding to the one or more indicia.

19. A method, comprising:
using a processor circuit, constructing a first image of a plane parallel to the surface of an ultrasonic imaging transducer, the plane corresponding to a locus at a specified depth within a first region of tissue, using information obtained from the imaging transducer;
using the processor circuit, obtaining information about a location of a vessel in the first image;
using the processor circuit, obtaining, from a second region of tissue, imaging information corresponding to loci in planes parallel to the surface of the transducer, the planes at depths automatically determined at least in part using the obtained information about the location of the vessel in the first image;
using the processor circuit, automatically determining an adjusted depth corresponding to the location of the vessel in the second region;
using the processor circuit, constructing a second image of a plane parallel to the surface of the transducer, the plane corresponding to the adjusted depth within the tissue; and
using the processor circuit, constructing a third image of a plane perpendicular to the surface of the imaging transducer, the third image including a cross-sectional view of the vessel, the third image determined using information about a series of constructed images corresponding to various depths of planes parallel to the surface of the imaging transducer;
wherein the first and second regions are offset from each other.

20. The method of claim 19, wherein the specified depth corresponding to the first image includes information obtained via a user input.

21. The method of claim 19, comprising presenting the constructed second image via a display.

22. The method of claim 19, wherein the first and second regions at least partially overlap with each other.

23. The method of claim 19, wherein the imaging transducer comprises an ultrasonic transducer array located externally to the tissue;
wherein constructing the first image includes:
insonifying the first region of tissue using the ultrasonic transducer array; and
in response to the insonification, obtaining echo information from the insonified first region of tissue; and
wherein obtaining imaging information from the second region of the tissue includes:
insonifying the second region of tissue and obtain echo information from the insonified second region of tissue, the echo information corresponding to loci in planes parallel to the surface of the transducer, the planes at depths automatically determined at least in part using the obtained information about the location of the vessel in the first image.

24. The method of claim 23, wherein automatically determining an adjusted depth corresponding to the location of the vessel in the second region includes:
obtaining imaging information including blood motion information;
estimating a depth corresponding to the center of the long axis of the vessel where the blood motion information indicates a maximum blood motion; and
assigning the estimated depth as the adjusted depth.

25. The method of claim 19, wherein obtaining information about a location of a vessel in the first image includes obtaining information about one or more of a vessel center, or a location of the vessel walls, via a user input.

26. The method of claim 25, wherein the information obtained via the user input includes one or more of a selection made via a keyboard, a mouse, a rotary control input, a touch-screen input, or a soft-key input located on or near a display.

27. The method of claim 25, wherein automatically determining an adjusted depth corresponding to the location of the vessel in the second region includes:
determining mean cross-sectional distances between the vessel walls corresponding to each of the scanned planes in the second region of tissue using an initial depth determined at least in part using the information about the vessel location obtained via the user input;
estimating a depth corresponding to a maximum mean cross-sectional distance using the determined mean cross-sectional distances; and
assigning the estimated depth as the adjusted depth.

28. The method of claim 25, wherein automatically determining an adjusted depth corresponding to the location of the vessel in the second region includes:
   determining a first depth using obtained imaging information indicative of a shallow boundary of the vessel, closer to the imaging transducer in depth than a deep boundary of the vessel;
   determining a second depth indicative of the deep boundary of the vessel;
   estimating a depth corresponding to the center of the long axis of the vessel between the shallow and deep boundaries; and
   assigning the estimated depth as the adjusted depth; and
   wherein one or more of the determining the first depth or determining the second depth includes using information about the vessel location obtained via the user input.

29. The method of claim 19, wherein determining the depths of one or more of the shallow or deep boundaries of the vessel include iteratively obtaining imaging information, and constructing images, corresponding to a variety of depths, until a bright reflection corresponding to an interface between the vessel and the surrounding tissue is detected.

30. The method of claim 29, comprising declaring an error if no bright reflection corresponding to an interface between the vessel and the surrounding tissue can be detected.

31. The method of claim 21, comprising displaying an indicator of the adjusted depth on or near the constructed second image via the display, the indicator including one or more of a bar-graph, an alphanumeric indicator, a color overlaying or otherwise comprising a portion of the constructed second image, or a line aligned with or overlaying the constructed second image.

32. The method of claim 21, comprising:
   obtaining imaging information including blood motion information;
   constructing a composite image including the vessel and a representation of blood motion corresponding to at least a portion of the vessel; and
   presenting the constructed image via the display.

33. The method of claim 19, comprising constructing a composite image including the first and second constructed images.

34. The method of claim 33, wherein constructing the composite image includes constructing a three-dimensional representation of the vessel.

35. The method of claim 33, wherein constructing the composite image includes constructing a two-dimensional representation of the vessel, including one or more indicia overlaying or aligned with the representation of the vessel, the one or more indicia indicating a depth of the vessel at one or more locations corresponding to the one or more indicia.

* * * * *